(12) United States Patent
Tang

(10) Patent No.: US 10,960,149 B2
(45) Date of Patent: Mar. 30, 2021

(54) FIXED-AMOUNT PRESSURIZED ATOMIZATION DEVICE

(71) Applicant: Gold Nanotech, Inc., Taipei (TW)

(72) Inventor: James Tang, Taipei (TW)

(73) Assignee: Gold Nanotech, Inc., Taipei (TW)

( * ) Notice: Subject to any disclaimer, the term of this patent is extended or adjusted under 35 U.S.C. 154(b) by 986 days.

(21) Appl. No.: 15/288,185

(22) Filed: Oct. 7, 2016

(65) Prior Publication Data

US 2018/0099104 A1    Apr. 12, 2018

(51) Int. Cl.
| | |
|---|---|
| *A61M 11/00* | (2006.01) |
| *A61M 39/22* | (2006.01) |
| *A61M 15/00* | (2006.01) |
| *B05B 17/06* | (2006.01) |
| *B05B 7/00* | (2006.01) |
| *B05B 7/24* | (2006.01) |
| *A61M 16/12* | (2006.01) |

(52) U.S. Cl.
CPC ...... *A61M 11/005* (2013.01); *A61M 15/0085* (2013.01); *A61M 39/22* (2013.01); *B05B 7/00* (2013.01); *B05B 7/2405* (2013.01); *B05B 17/0607* (2013.01); *A61M 16/127* (2014.02); *A61M 2039/226* (2013.01)

(58) Field of Classification Search
CPC ....... B05B 7/02; B05B 7/0416; B05B 7/0458; B05B 7/0483; B05B 7/24; B05B 7/2402; B05B 7/2405; B05B 7/2408; B05B 7/2421; B05B 17/06; B05B 17/0607; B05B 17/170638; B05B 17/0646; A61M 11/005; A61M 39/22; A61M 39/226; A61M 15/001; A61M 15/002; A61M 15/0085
USPC .......... 239/102.1, 102.2, 310, 311, 315, 316, 239/345, 346, 376, 407, 398, 409, 433
See application file for complete search history.

(56) References Cited

U.S. PATENT DOCUMENTS

| | | | |
|---|---|---|---|
| 6,257,000 B1 * | 7/2001 | Wang | F17C 7/00 222/3 |
| 2014/0116426 A1 * | 5/2014 | Mullinger | A61M 11/005 128/200.14 |
| 2014/0334804 A1 * | 11/2014 | Choi | A61M 15/06 392/404 |
| 2017/0095052 A1 * | 4/2017 | Nagata | A45D 34/04 |

* cited by examiner

Primary Examiner — Jason J Boeckmann

(57) ABSTRACT

A liquid introducing device transfers a fixed amount of liquid medicine into atomized particles. The liquid medicine is connected to the liquid introducing device which allows the users to quickly replace the bottles and avoid cross infection between different medicines. The liquid introducing device is powered by electric power to atomize the liquid quickly. The liquid introducing device includes a chamber which cooperated with an electro-magnetic valve switch which controls a fixed amount of air in the chamber such that the fixed amount of the air can be pressurized and output stably. The pressurized air passes through the tube without delay and loss.

7 Claims, 8 Drawing Sheets

FIXED-AMOUNT PRESSURIZED ATOMIZATION DEVICE

BACKGROUND OF THE INVENTION

1. Field of the Invention

The present invention relates to a liquid introducing device, and more particularly, to a liquid introducing device which transfers a fixed amount of liquid into atomized particles. The liquid introducing device is easily assembled, dis-assembled and replacement.

2. Description of the Prior Art

There are different types of injection devices are available in the market, nevertheless, only few of the injection devices are needle-less to deliver medicine to the dermis. The most commonly used injection devices generally include a housing which includes a chamber or a housing for carrying medicine. A house is connected to the injection device to provide pressurized air which injects the medicine to the dermis of the patients. When the operators pull the trigger, the medicine is injected out from the injection device in the shape of a column and delivered to the dermis. This causes injury in the skin and the patients feel pain for the injection. When replacing the medicine of the injection devices, the injection devices have to be sterilized completely by multiple steps. Another injection devices use pressure to atomize the medicine, however, the medicine cannot be precisely delivered to the dermis, so that the result is not satisfied.

Besides, the injection devices involve too many parts which are difficult to be assembled together. Due to the complicated shapes of the parts, the sterilization process cannot be finished as desired, especially to those small pipes or ducts.

In addition, it is not convenient to install the medicine or to replace the medicine, it takes a lot of time. Another problem is that it is difficult to remove all of the debris of the previous medicine in the injection devices.

Furthermore, the replacement or installation of the liquid medicine bottles is not convenient and efficient. There could be debris left in the device and the risk of cross infection exists and this is not safe for the patients.

The present invention intends to provide a liquid introducing device which transfers a fixed amount of liquid into atomized articles, and the liquid introducing device is easily assembled, dis-assembled and replacement.

SUMMARY OF THE INVENTION

The present invention relates to a liquid introducing device and comprises an introducing unit having a housing. The housing has a removable cap at the first end thereof. A bottle for receiving liquid therein is connected to the housing and located above the removable cap. A second end of the housing has an air introducing port which is connected with an exterior air source. A connection wire for being connected exterior power source is connected to the second end of the housing. The housing has a tube made by way of Venturi principle, a clamping unit, a chamber, and a circuit control unit received therein. The tube is integrally connected with the clamping unit. One end of the tube is connected to the first end of the chamber, and the circuit control unit is located beside the chamber. The second end of the chamber is connected with the air introducing port. The circuit control unit is electrically connected to the connection wire.

Preferably, a base and an engaging member are connected to the outside of the tube, wherein the base has a vibration plate which includes multiple orifices. The base has a passage defined centrally therein which communicates with the tube. A circuit board is inserted into the engaging member and electrically connected to the vibration plate.

Preferably, the clamping unit is connected to the base and has a clamp and a positioning portion so that the bottle is positioned and released by the clamp and the positioning portion.

Preferably, the circuit control unit has a spring connector which secures or separates the circuit board.

Preferably, the circuit control unit has an electro-magnetic valve switch and a valve opening, wherein the valve opening is located between the tube and the chamber, and controlled by the electro-magnetic valve switch so as to control the release of air in the chamber. The circuit control unit controls the amount of the air to be released. The liquid is oscillated and atomized by the vibration plate, and the air is mixed with the atomized liquid. The mixture is then ejected through the tube.

Preferably, the exterior air source connected to the air introducing port includes a movable air source and a fixed air source.

Preferably, the diameter of each of the orifices of the vibration plate is below 25 μm, and the number of the orifices is below 800.

Preferably, the movable air source includes an arm wrap, a securing member, an air source control member, a pressurized air bottle and a pressure regulating valve. The pressure regulating valve has an air outlet which is connected to the air introducing port of the introducing unit by a pipe.

The primary object of the present invention is to provide a liquid introducing device which combines the medicine bottle and the introducing unit to quickly atomize the liquid medicine into small particles. The replacement of the bottles is quick and efficient. The risk of cross infection is eliminated.

Another object of the present invention is to provide a liquid introducing device wherein an electric power source is connected with the device so that the wiring is simplified and the time required to atomize the liquid medicine is shortened.

Yet another object of the present invention is to provide a liquid introducing device wherein the device includes a chamber which is cooperated with an electro-magnetic valve switch so as to pre-store the air in the chamber and the air is output under stable pressure such that when the air passes through the tube, the loss and delay of the air in the tube are reduced.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
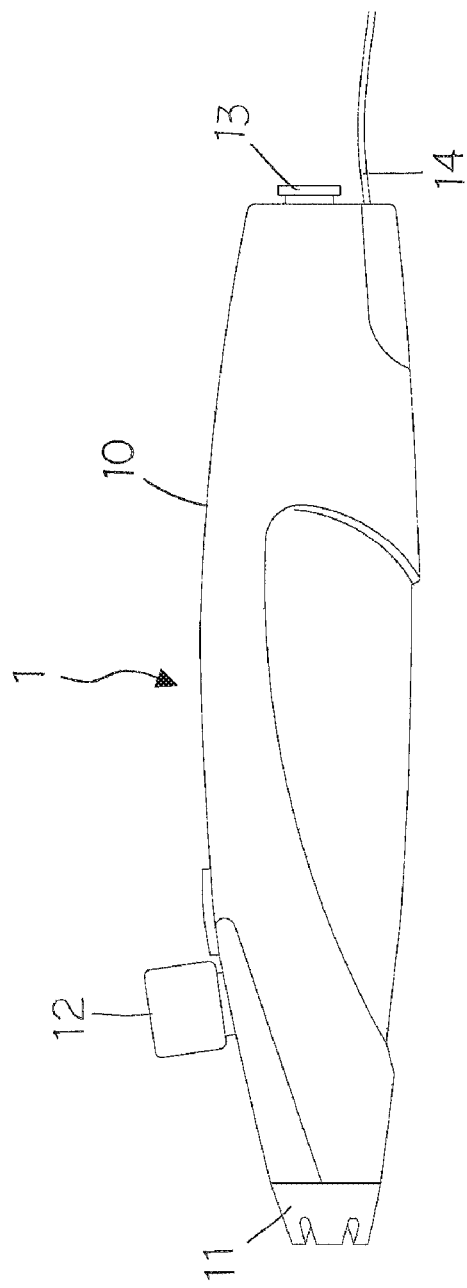
FIG. 1 is a perspective view to show the liquid introducing device of the present invention.

Referring to FIGS. 1 to 8, the liquid introducing device of the present invention is designed to be used in the fields of medical and cosmetic treatments and comprises an introducing unit 1 which has a housing 10.

The housing 10 has a removable cap 11 at the first end thereof, and a hole is defined in the removable cap 11 for the injection of the atomized mixture of liquid and air. The removable cap 11 can be easily removed for checking the interior of the housing 10. A bottle 12 for receiving liquid or medicine therein is connected to the housing 10 and located above the removable cap 11. The second end of the housing 10 has an air introducing port 13 which is connected with an exterior air source. A connection wire 14 is connected to the second end of the housing 10 so as to be connected to an exterior power source (not shown).

Figure 2:
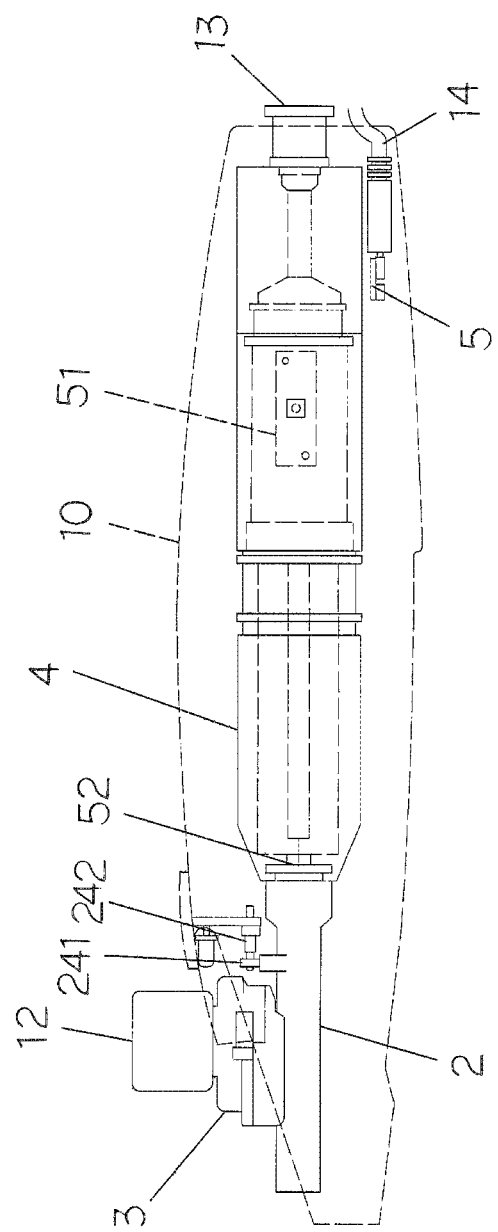
FIG. 2 shows the parts in the liquid introducing device of the present invention.
Figure 3:
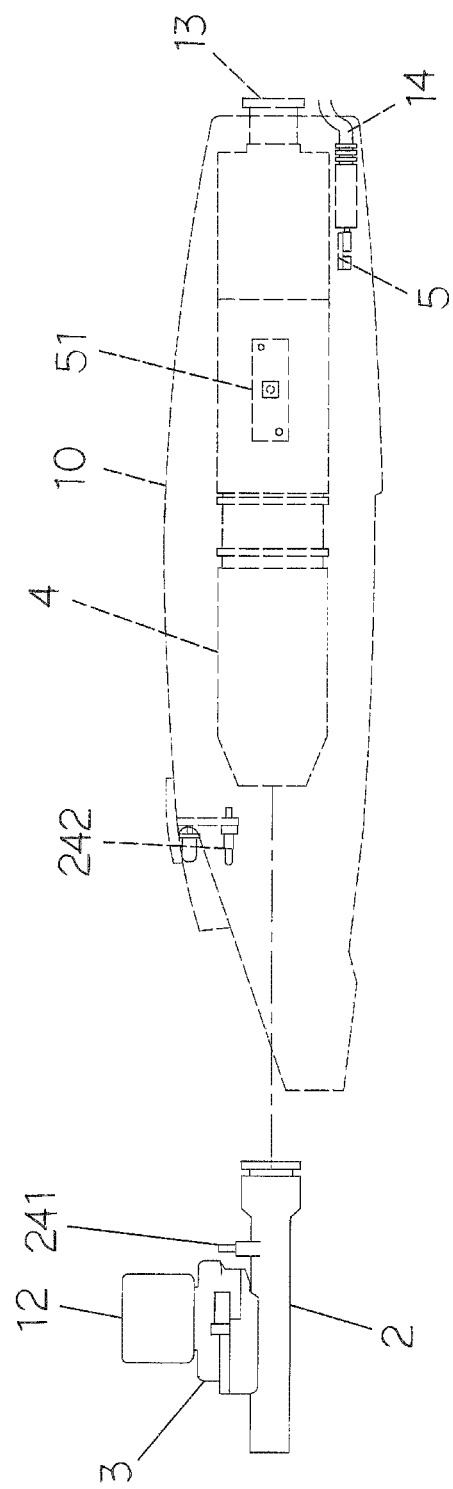
FIG. 3 is an exploded plan view of the liquid introducing device of the present invention.

As shown in FIGS. 2 and 3, the housing 10 having a tube 2, a clamping unit 3, a chamber 4, and a circuit control unit 5 received therein. The tube 2 is integrally connected with the clamping unit 3. The clamping unit 3 is connected to the bottle 12. One end of the tube 2 is connected to the first end of the chamber 4. The circuit control unit 5 is located beside the chamber 4. The second end of the chamber 4 is connected with the air introducing port 13. The circuit control unit 5 is electrically connected to the connection wire 14.

Figure 4:
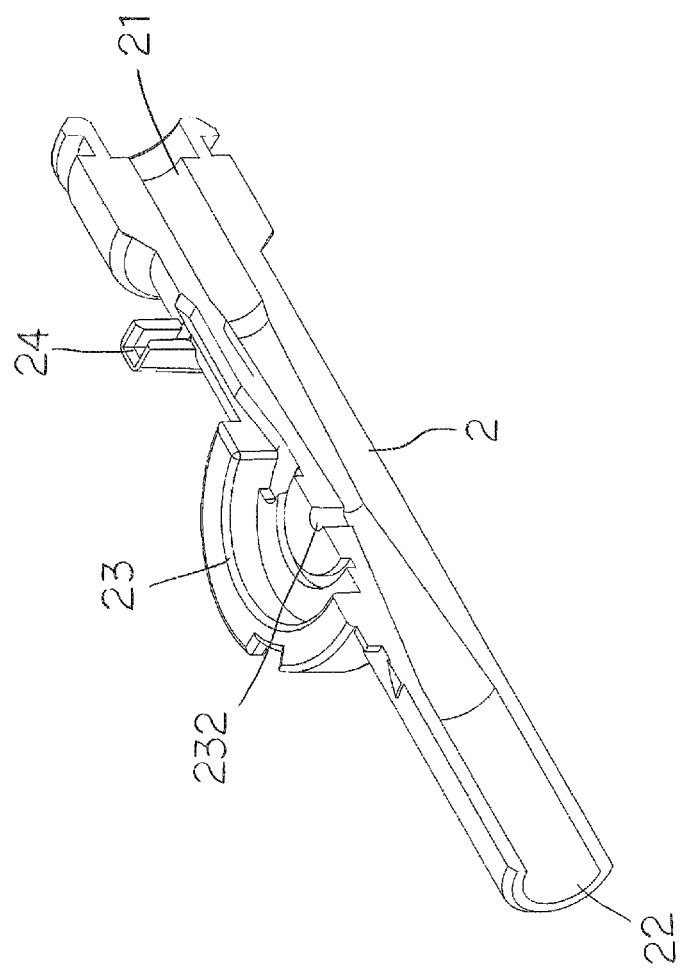
FIG. 4 shows a half portion of the tube of the liquid introducing device of the present invention.
Figure 5:
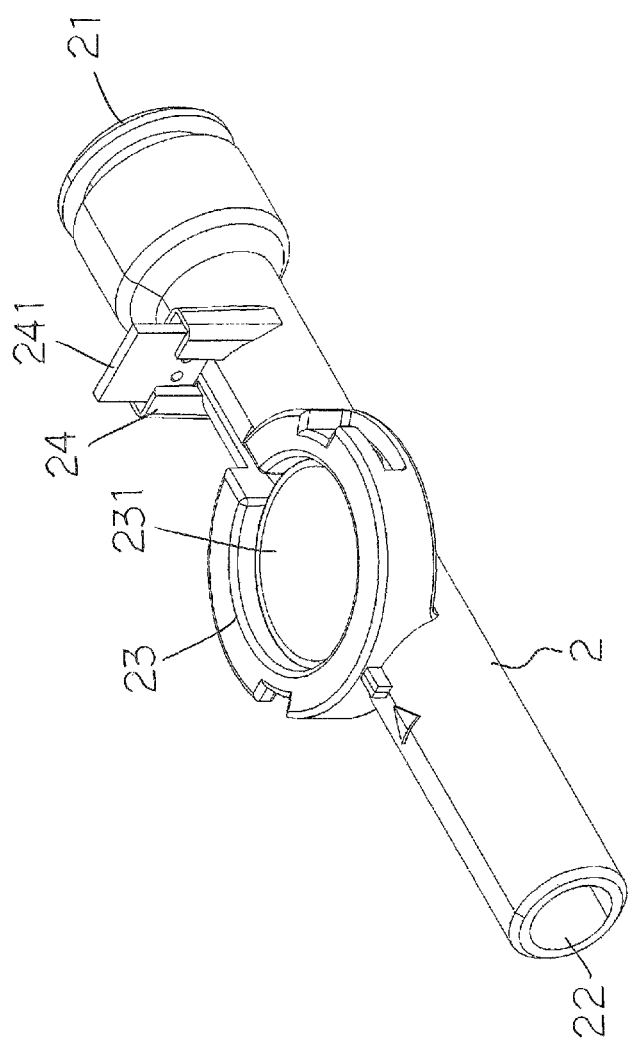
FIG. 5 is a perspective view to show the tube of the liquid introducing device of the present invention.

As shown in FIGS. 4 and 5, the tube 2 is a Venturi tube and includes an air inlet 21 defined in one end thereof, and a liquid outlet 22 is defined in the other end thereof. A base 23 and an engaging member 24 are connected to the outside of the tube 2. The base 23 has a vibration plate 231 which includes multiple orifices. The base 23 has a passage 232 defined centrally therein which communicates with the tube 2. The circuit board 241 is inserted into the engaging member 24 and electrically connected to the vibration plate 231.

The diameter of each of the orifices of the vibration plate 231 is below 25 µm, and the number of the orifices is below 800. The vibration plate 231 vibrates by ultra-sonic waves so as to oscillate the liquid to be atomized particles which are suitable for being absorbed by patients' skin.

Figure 6:
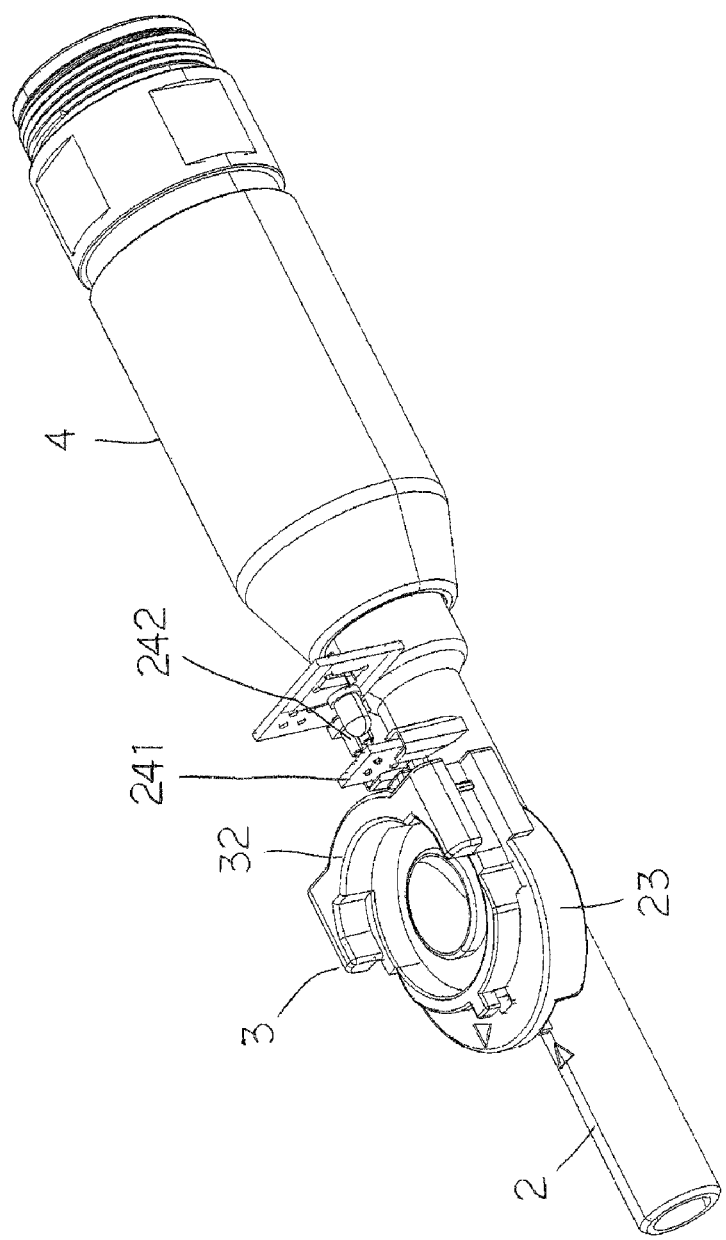
FIG. 6 is a perspective view to show the combination of the tube, the clamping unit and the chamber of the liquid introducing device of the present invention, wherein the clamp is not installed.
Figure 7:
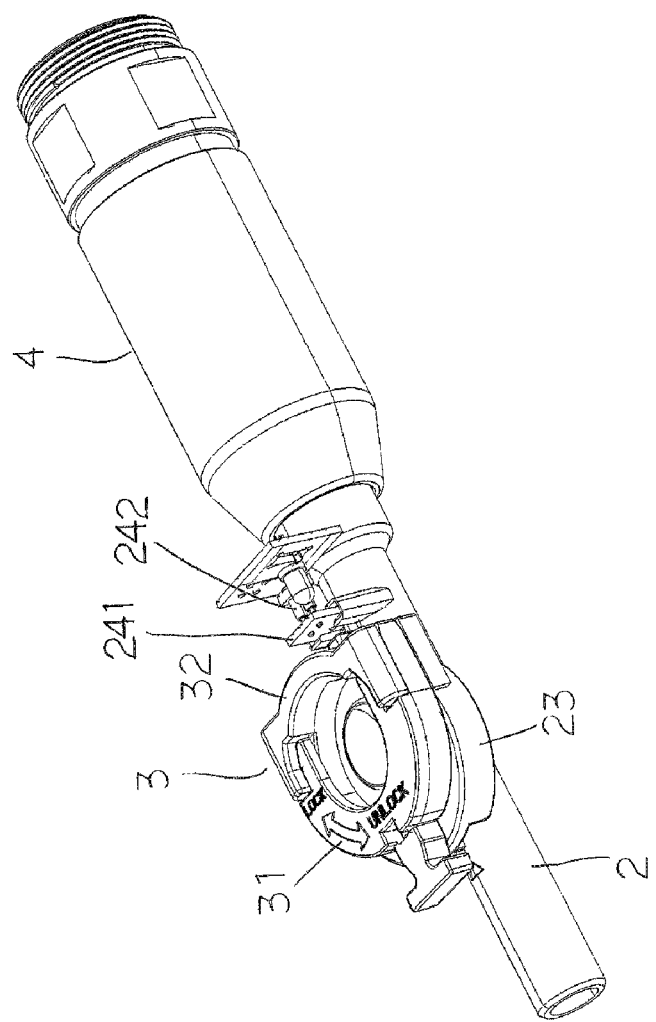
FIG. 7 is a perspective view to show the combination of the tube, the clamping unit and the chamber of the liquid introducing device of the present invention, wherein the clamp is installed.

As shown in FIGS. 6 and 7, the clamping unit 3 is connected to the base 23 and has a clamp 31 and a positioning portion 32 so that the bottle 12 is positioned and released by the clamp 31 and the positioning portion 32 quickly. In this embodiment, the clamp 31 is a semi-circular and Y-shaped clamp. The positioning portion 32 is a semi-circular portion to be cooperated with the clamp 31. FIG. 6 shows that when the clamping unit 3 is opened and the clamp 31 is removed. FIG. 7 shows that when the clamping unit 3 is closed, wherein the clamp 31 and the positioning portion 32 are connected to each other.

As shown in FIGS. 2 and 3, the chamber 4 is connected between the air inlet 21 of the tube 2 and the air introducing port 13, wherein the air introducing port 13 is connected to the exterior air source. The air in the chamber 4 is kept under a pre-set pressure, and the stable pressure of the pressurized air reduces loss and delay when passing through the tube 2.

The circuit control unit 5 is located beside the chamber 4 and electrically connected with the connection wire 14 such that the exterior power source provides electric power to the circuit control unit 5. The circuit control unit 5 has an electro-magnetic valve switch 51, a valve opening 52 and a spring connector 242. The valve opening 52 is located between the tube 2 and the chamber 4, and controlled by the electro-magnetic valve switch 51 so as to control the release of air in the chamber 4. The circuit control unit 5 controls the amount of the air to be released. The spring connector 242 is designed to be in contact with the circuit board 241 or to be separated from the circuit board 241.

When in operation, the circuit control unit 5 is powered by the exterior power source and introduces air from the exterior air source into the device from the air introducing port 13. In the same time, the electro-magnetic valve switch 51 opens the valve opening 52 to release the pre-stored air in the chamber 4 so as to maintain the air under stable pressure. The vibration plate 231 vibrates by the ultra-sonic waves to atomize the liquid released from the bottle 12, and the atomized liquid is then sent to the tube 2, and the air released from the chamber 4 mixes the atomized liquid, the mixture is then ejected from the tube 2.

When the bottle 12 needs to be replaced, the tube 2 together with the bottle 12 are separated from the chamber 4. For safety and sanitation concern, the tube 2 and the bottle 12 are disposable.

When the tube 2 is removed, the circuit board 241 is separated from the spring connector 242 so that the circuit is opened. When the new tube 2 and bottle 12 are installed and connected to the chamber 4, the circuit board 241 is connected to the spring connector 242 again, and the circuit is re-activated automatically.

It is noted that the exterior air source that is connected to the air introducing port 13 can be a movable air source 6 or a fixed air source. The fixed air source is the pressurized steel bottle as commonly seen, which is heavy and difficult to move. The fixed air source is connected to the air introducing port 13 by a proper pipe.

Figure 8:
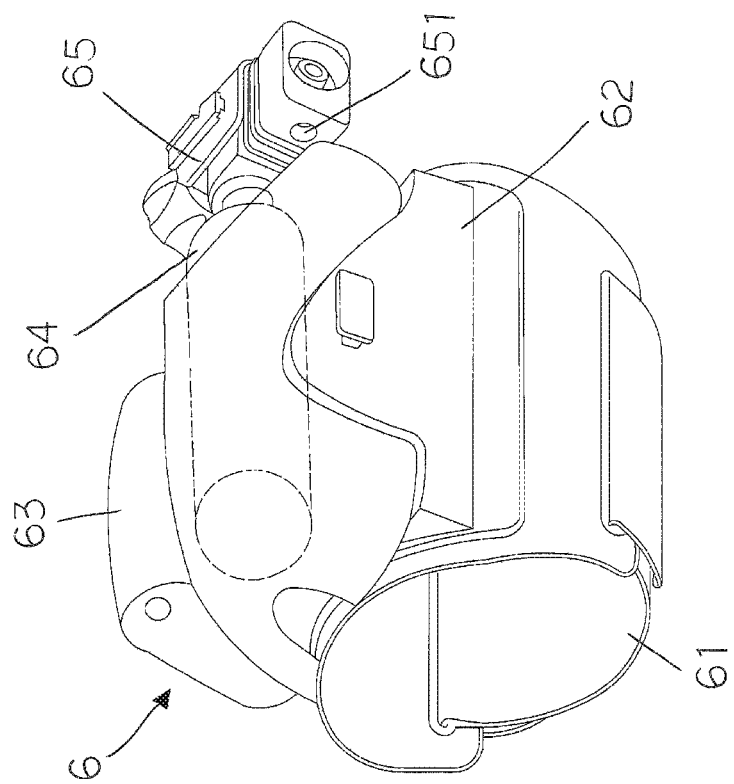
FIG. 8 shows the air pressure source of the liquid introducing device of the present invention.

As shown in FIG. 8, the movable air source 6 includes an arm wrap 61, a securing member 62, an air source control member 63, a pressurized air bottle 64 and a pressure regulating valve 65. The pressure regulating valve 65 has an air outlet 651 which is connected to the air introducing port 13 of the introducing unit 1 by a pipe. By using the arm wrap 61, the movable air source 6 is attached to the patient's arm and provides convenient and mobile feature.

The advantages of the present invention are that the liquid introducing device combines the medicine bottle and the introducing unit so that the replacement of the bottles is quick and efficient, and the risk of cross infection is eliminated.

The liquid introducing device is connected with an electric power source so that the wiring is simplified and the time required to atomize the liquid medicine is shortened.

The liquid introducing device includes a chamber which is cooperated with an electro-magnetic valve switch so as to pre-store the air in the chamber and the air is output under stable pressure such that when the air passes through the tube, the loss and delay of the air in the tube are reduced.

While we have shown and described the embodiment in accordance with the present invention, it should be clear to those skilled in the art that further embodiments may be made without departing from the scope of the present invention.

What is claimed is:

1. A liquid introducing device comprising:
an introducing unit having a housing, the housing having a removable cap at a first end thereof, a bottle for receiving liquid therein being connected to the housing and located above the removable cap, a second end of the housing having an air introducing port which is connected with an exterior air source, a connection wire adapted to be connected to an exterior power source at the second end of the housing, the housing having a tube, a seat, a chamber, and a circuit control unit received therein, the tube integrally connected with the seat, one end of the tube connected to a first end of the chamber, the circuit control unit located beside the chamber, a second end of the chamber connected with the air introducing port, the circuit control unit electrically connected to the connection wire,
wherein the seat has a clamp and a wall member whereby the bottle is positioned to directly contact the clamp and the wall member and released from the clamp and the wall member; and
wherein a base is connected to an outside of the tube, the base having a vibration plate which includes multiple orifices, the base having a passage defined centrally therein which communicates with the tube.

2. The liquid introducing device as claimed in claim 1, wherein a frame is connected to the outside of the tube, a circuit board held by the frame and electrically connected to the vibration plate.

3. The liquid introducing device as claimed in claim 2, wherein the seat is connected to the base.

4. The liquid introducing device as claimed in claim 2, wherein the circuit control unit has a spring connector which secures or separates the circuit board.

5. The liquid introducing device as claimed in claim 1, wherein the circuit control unit has an electro-magnetic valve switch and a valve opening, the valve opening being located between the tube and the chamber, and controlled by the electro-magnetic valve switch so as to control a release of air in the chamber, the circuit control unit controlling an amount of the air to be released.

6. The liquid introducing device as claimed in claim 1, wherein the exterior air source connected to the air introducing port includes a movable air source.

7. The liquid introducing device as claimed in claim 6, wherein the movable air source includes an arm wrap, a pressurized air bottle receiving member, an air source control member, a pressurized air bottle and a pressure regulating valve, the pressure regulating valve has an air outlet which is connected to the air introducing port of the introducing unit.

\* \* \* \* \*